(12) United States Patent
Bergström et al.

(10) Patent No.: US 9,904,562 B2
(45) Date of Patent: Feb. 27, 2018

(54) EVENT-DRIVEN TRANSITIONS IN ABSORBENT ARTICLE MANAGEMENT

(71) Applicant: SCA Hygiene Products AB, Göteborg (SE)

(72) Inventors: Per Bergström, Göteborg (SE); Christer Olofsson Ranta, Västra Frölunda (SE); Björn Ålsnäs, Onsala (SE); Mattias Bosaeus, Kallered (SE)

(73) Assignee: SCA HYGIENE PRODUCTS AB, Göteborg (SE)

( * ) Notice: Subject to any disclaimer, the term of this patent is extended or adjusted under 35 U.S.C. 154(b) by 0 days.

(21) Appl. No.: 14/787,583

(22) PCT Filed: Apr. 30, 2013

(86) PCT No.: PCT/EP2013/059047
§ 371 (c)(1),
(2) Date: Oct. 28, 2015

(87) PCT Pub. No.: WO2014/177204
PCT Pub. Date: Nov. 6, 2014

(65) Prior Publication Data
US 2016/0170776 A1 Jun. 16, 2016

(51) Int. Cl.
*G06F 9/445* (2006.01)
*A61F 13/42* (2006.01)
(Continued)

(52) U.S. Cl.
CPC .......... *G06F 9/44505* (2013.01); *A61F 13/42* (2013.01); *G06F 1/3212* (2013.01); *H04L 67/12* (2013.01); *A61F 2013/424* (2013.01)

(58) Field of Classification Search
CPC .... G06F 9/44505; G06F 1/3212; A61F 13/42; A61F 2013/424; H04L 67/12
See application file for complete search history.

(56) References Cited

U.S. PATENT DOCUMENTS 6,419,636 B1 * 7/2002 Young ............... A61B 5/015
 600/372
7,053,781 B1 * 5/2006 Haire ............... A61F 13/42
 340/573.5
(Continued)

FOREIGN PATENT DOCUMENTS

JP H07-239990 9/1995
JP 2004-529730 9/2004
(Continued)

OTHER PUBLICATIONS

English-language translation of an Office Action dated Dec. 5, 2016 issued in corresponding Japanese patent application No. 2016-509308 (5 pages).
(Continued)

*Primary Examiner* — Robert Cassity
*Assistant Examiner* — Chad Erdman
(74) *Attorney, Agent, or Firm* — Drinker Biddle & Reath LLP

(57) ABSTRACT

A method of operating a datalogger adapted for logging sensor data from an absorbent article having at least one sensor element and the datalogger are described. The method includes: determining an external event; and on determination of the external event, transitioning from a first operating condition to a second operating condition. The external event can be an event selected from: a disconnection event in which the datalogger is disconnected from the absorbent article; a connection event in which the datalogger is connected to an absorbent article; a charge event in which the datalogger is connected to a charging station; and a user interaction event in which the user interacts with a user interface element of the datalogger. The first and second operation conditions can be selected from: a datalogging
(Continued)

condition; a standby condition; a status notification condition; and a data transmission condition.

18 Claims, 5 Drawing Sheets

(51) Int. Cl.
*G06F 1/32* (2006.01)
*H04L 29/08* (2006.01)

(56) References Cited

U.S. PATENT DOCUMENTS

| | | |
|---|---|---|
| 7,250,547 B1 | 7/2007 | Hofmeister et al. |
| 7,977,529 B2 | 7/2011 | Bergman et al. |
| 9,480,846 B2 * | 11/2016 | Strother .................. A61N 1/08 |
| 2005/0156744 A1 | 7/2005 | Pires |
| 2007/0252710 A1 * | 11/2007 | Long ...................... A61F 13/42 |
| | | 340/573.5 |
| 2007/0252714 A1 | 11/2007 | Rondoni et al. |
| 2007/0270921 A1 | 11/2007 | Strother et al. |
| 2008/0243099 A1 | 10/2008 | Tippey et al. |
| 2009/0069749 A1 * | 3/2009 | Miller .................. A61M 5/1413 |
| | | 604/151 |
| 2011/0263952 A1 | 10/2011 | Bergman et al. |
| 2011/0295619 A1 | 12/2011 | Tough |
| 2012/0101630 A1 * | 4/2012 | Daya .................... G06F 19/325 |
| | | 700/231 |
| 2012/0215075 A1 * | 8/2012 | Surace ................ A61B 5/0002 |
| | | 600/301 |
| 2012/0268278 A1 * | 10/2012 | Lewis .................... A61F 13/42 |
| | | 340/573.5 |

FOREIGN PATENT DOCUMENTS

| | | |
|---|---|---|
| JP | 2008-136859 | 6/2008 |
| JP | 2009-535130 | 10/2009 |
| JP | 2013-509280 | 3/2013 |
| KR | 2012-0009644 A | 2/2012 |
| WO | WO-96/14813 A1 | 5/1996 |
| WO | WO-00/00144 A2 | 1/2000 |
| WO | WO 02/101679 | 12/2002 |
| WO | WO-2004/100763 A2 | 11/2004 |
| WO | WO-2005/017683 A2 | 2/2005 |
| WO | WO-2006/047815 A1 | 5/2006 |
| WO | WO 2007/128038 | 11/2007 |
| WO | WO-2008/038167 A2 | 4/2008 |
| WO | WO-2011/054045 A1 | 5/2011 |
| WO | WO-2011/126497 A1 | 10/2011 |
| WO | WO-2011/156862 A1 | 12/2011 |

OTHER PUBLICATIONS

English-language translation of an Russian Office Action dated Apr. 12, 2017 issued in corresponding Russian patent application No. 2015150397 (3 pages).
Canadian Office Action dated May 2, 2017 issued in corresponding Canadian patent application No. 2,909,185 (4 pages).
Japanese Decision on Grant dated Jul. 10, 2017 issued in corresponding Japanese patent application No. 2016-509308 (3 pages) and its English-language translation thereof (3 pages).
European examination report dated Jun. 13, 2017 issued in corresponding European patent application No. 13 720 907.8 (7 pages).

* cited by examiner

EVENT-DRIVEN TRANSITIONS IN ABSORBENT ARTICLE MANAGEMENT

CROSS-REFERENCE TO PRIOR APPLICATION

This application is a § 371 National Stage Application of PCT/EP2013/059047 filed Apr. 30, 2015, which is incorporated herein in its entirety.

TECHNICAL FIELD

The present disclosure relates to a method of operating a datalogger adapted for logging sensor data from an absorbent article having sensor elements, a datalogger, an absorbent article, and an incontinence management system suitable for implementing the method.

Especially, the present disclosure relates to a method of operating a datalogger which is able to provide an absorbent article, such as a diaper, a sanitary towel, an incontinence garment, a medical dressing and the like, with sensing and datalogging capabilities. Especially, the method provides the datalogger with an ability to detect external events and to transition between internal states on the basis of those external events.

TECHNICAL BACKGROUND

Absorbent articles, such as diapers, sanitary towels, incontinence garments, medical dressings and the like, have widespread utility in both domestic and institutional settings for such purposes as the care of infants, the management of menstrual discharge, the management of bodily efflux or exudate and the management of incontinence. However, a known problem associated with the use of absorbent articles is that the articles have a finite capacity for absorption which, if exceeded, will cause the absorbent article to become ineffective, e.g. to leak, or at least to fail to absorb further.

Therefore, users of such articles, or their carers, must predict when an absorbent article is nearing its absorbent capacity and must then take steps to replace the article before capacity is reached. In situations where there are many users of such absorbent articles but relatively fewer carers, such as in institutional settings, the management of the capacity of the various absorbent articles in use becomes a significant administrative burden.

Since absorbent articles are available in a variety of absorbent capacities, the user or carer must also determine, from those products which are available, which capacity of article to select. For example, in some circumstances it may be preferable to select an article of a lower capacity which is changed more frequently in contrast to an article of relatively larger capacity which is changed less frequently. Factors influencing this choice will be the nature of the absorption required, i.e. whether intermittent large quantities or a continuous smaller rate, as well as the total volume expected to be absorbed during a given period of time.

It can be very difficult for a user or carer to accurately predict or determine the state of an absorbent article, in terms both of utilised absorbent capacity and the need for the article to be replaced. Even where the absorbent demands on the article are reasonably predictable, a period of record-keeping and experimentation is required before a pattern may be established and appropriate absorbent articles provided.

Systems which are able to alert the user or carer to saturation or impending saturation of the absorbent article are therefore of benefit. Furthermore, systems which are able to monitor the usage pattern of a particular absorbent article, and of a series of absorbent articles associated with a particular individual, over a period of time, are of particular benefit.

Such systems may take the form of an absorbent article having embedded sensors which connect to a logger unit to monitor and record the sensor data over time. The sensors can, for example, be moisture sensors. When the absorbent capacity of the absorbent article is approached or exceeded, the user or the carer can be notified, on the basis of the recorded sensor data, that the absorbent article requires replacement.

Additionally, data obtained from a particular user over time can be used to monitor both the health of the user and the appropriateness of the absorbent article for that user over an extended period and can be used to provide better information for the care of the user. For example, an event, such as an incontinence event, leading to saturation of the article can be predicted and action, such as toileting action, taken before the event occurs.

One exemplary system is shown in FIG. 1, in which an absorbent article 400, exemplified here as a diaper and having a waistband 410 and an absorbent area 420, is provided with a logger unit 300 attached to the waistband 410 and having sense wires 430 extending from the logger unit 300 running through the absorbent area. The sense wires 430 may be used to detect moisture, for example by detecting changes in the conductivity between the wires. The sense wires may be only partly exposed to the absorbent area, for example by providing insulation, to localise the region of sensing. The particular wiring pattern depicted is wholly exemplary, and will be selected according to the sensing requirements.

The logger unit 300, including data-logging electronics such as a power source, processor, memory, instruction store, data store, communications bus, and data link interface, which cooperate to store, process, and/or forward the data derived from sense wires, is connected by data link 500 to a data receiver 600. In the example of FIG. 1, data link 500 is a wireless data link, and data receiver 600 is a wireless data receiver. However, in one alternative, data link 500 can be provided over the cellular telephone network, in which case data receiver 600 may be implemented as a cellular base station.

The data received at data receiver 600 is then transmitted by a further data link 700 to data processing equipment 800, exemplified as computer terminal 810 and output device 820 mutually connected by data link 830. Here, the computer terminal 810, which is an example of a general purpose data processing device, conducts processing on the sensor data received from the logger unit 300 via data links 500 and 700 and data receiver 600 and takes action based on the same, for example by outputting alerts, predictions, or statistics via output device 820. Here, the output device is shown as a line printer, but could, for example, be another form of hard copy printer, a visual display unit, a visual alarm panel, or an audio output device, without limitation.

Such a system may provide a powerful tool for the management of users of absorbent articles. For the convenience and comfort of the users, such a system should be as predictably and unobtrusive as possible in use. However, during the operation of such a system, conditions may occur that require action outside the usual datalogging process to be taken to ensure the continued correct operation of the system. A tension therefore exists between the requirement to be predictable in operation and unobtrusive to a user and the requirement to respond appropriately to a condition requiring action to be taken.

SUMMARY

According to a first aspect of the present disclosure, there is provided a method of operating a datalogger adapted for logging sensor data from an absorbent article having at least one sensor element, the method including: determining an external event; and on determination of the external event, transitioning from a first operating condition to a second operating condition.

In some embodiments, the external event is an event selected from: a disconnection event in which the datalogger is disconnected from the absorbent article; a connection event in which the datalogger is connected to an absorbent article; a charge event in which the datalogger is connected to a charging station; and a user interaction event in which the user interacts with a user interface element of the datalogger.

In some embodiments, the first and second operation conditions are selected from: a datalogging condition; a standby condition; a status notification condition; and a data transmission condition.

In some embodiments, the datalogger is battery powered and the status notification condition is a low battery notification condition.

In some embodiments, the datalogging condition includes the transmission of sensor data over a data link, and wherein the status notification condition is a data link failure condition.

In some embodiments, the datalogging condition includes the storage of sensor data in a memory internal to the datalogger and the transmission of stored sensor data at predetermined intervals over a data link, and the data transmission condition is a flush condition in which sensor data stored in the memory is transmitted over the data link at other than a predetermined interval of the datalogging condition.

In some embodiments, the method further includes transitioning from the second operating condition to a third operating condition on determination of a further event.

In some embodiments, the further event is an internal event selected from the expiry of a timer associated with the second operating condition; the completion of a process associated with the second operating condition; and a change in status of an internal device.

In some embodiments, the further event is an external event selected from: a disconnection event in which the datalogger is disconnected from the absorbent article; a connection event in which the datalogger is connected to an absorbent article; a charge event in which the datalogger is connected to a charging station; and a user interaction event in which the user interacts with a user interface element of the datalogger.

In some embodiments, the determination of the external event includes detection of a change in state of an electrical circuit of the datalogger that is responsive to an external event.

In some embodiments, the determination of the external event includes detection of at least one of: a change in state of at least one electrical contact on the exterior of the datalogger; a change in state of at least one sensor on the exterior of the datalogger; or a change in state of at least one switch on the exterior of the datalogger.

According to a second aspect of the present disclosure, there is provided a datalogger adapted for logging sensor data from an absorbent article having at least one sensor element, the datalogger including: a processor configured to determine an external event and, on determination of the external event, to transition from a first operating condition to a second operating condition.

In some embodiments, the external event is an event selected from: a disconnection event in which the datalogger is disconnected from the absorbent article; a connection event in which the datalogger is connected to an absorbent article; a charge event in which the datalogger is connected to a charging station; and a user interaction event in which the user interacts with a user interface element of the datalogger.

In some embodiments, the first and second operation conditions are selected from: a datalogging condition; a standby condition; a status notification condition; and a data transmission condition.

In some embodiments, the datalogger further includes a battery and the status notification condition is a low battery notification condition.

In some embodiments, the datalogger includes a transmitter and the datalogging condition includes the transmission of sensor data over a data link, and wherein the status notification condition is a data link failure condition.

In some embodiments, the datalogger further includes: a memory adapted to store sensor data; and a transmitter, the datalogging condition includes the storage of sensor data in the memory and the transmission of stored sensor data at predetermined intervals with the transmitter, and the data transmission condition is a flush condition in which sensor data stored in the memory is transmitted with the transmitter at other than a predetermined interval of the datalogging condition.

In some embodiments, the processor is configured to transition from the second operating condition to a third operating condition on determination of a further event.

In some embodiments, the further event is an internal event selected from the expiry of a timer associated with the second operating condition; the completion of a process associated with the second operating condition; and a change in status of an internal device.

In some embodiments, the further event is an external event selected from: a disconnection event in which the datalogger is disconnected from the absorbent article; a connection event in which the datalogger is connected to an absorbent article; a charge event in which the datalogger is connected to a charging station; and a user interaction event in which the user interacts with a user interface element of the datalogger.

In some embodiments, the determination of the external event includes detection of a change in state of an electrical circuit of the datalogger that is responsive to an external event.

In some embodiments, the determination of the external event includes detection of at least one of: a change in state of at least one electrical contact on the exterior of the datalogger; a change in state of at least one sensor on the exterior of the datalogger; and a change in state of at least one switch on the exterior of the datalogger.

BRIEF DESCRIPTION OF THE DRAWINGS

To better understand embodiments of the present invention, and to show how the same may be put into effect, reference will be made, by way of example only, to the accompanying Drawings, in which.

DETAILED DESCRIPTION OF PARTICULAR EMBODIMENTS

Embodiments of the present invention will now be described with reference to the figures.

Figure 1:
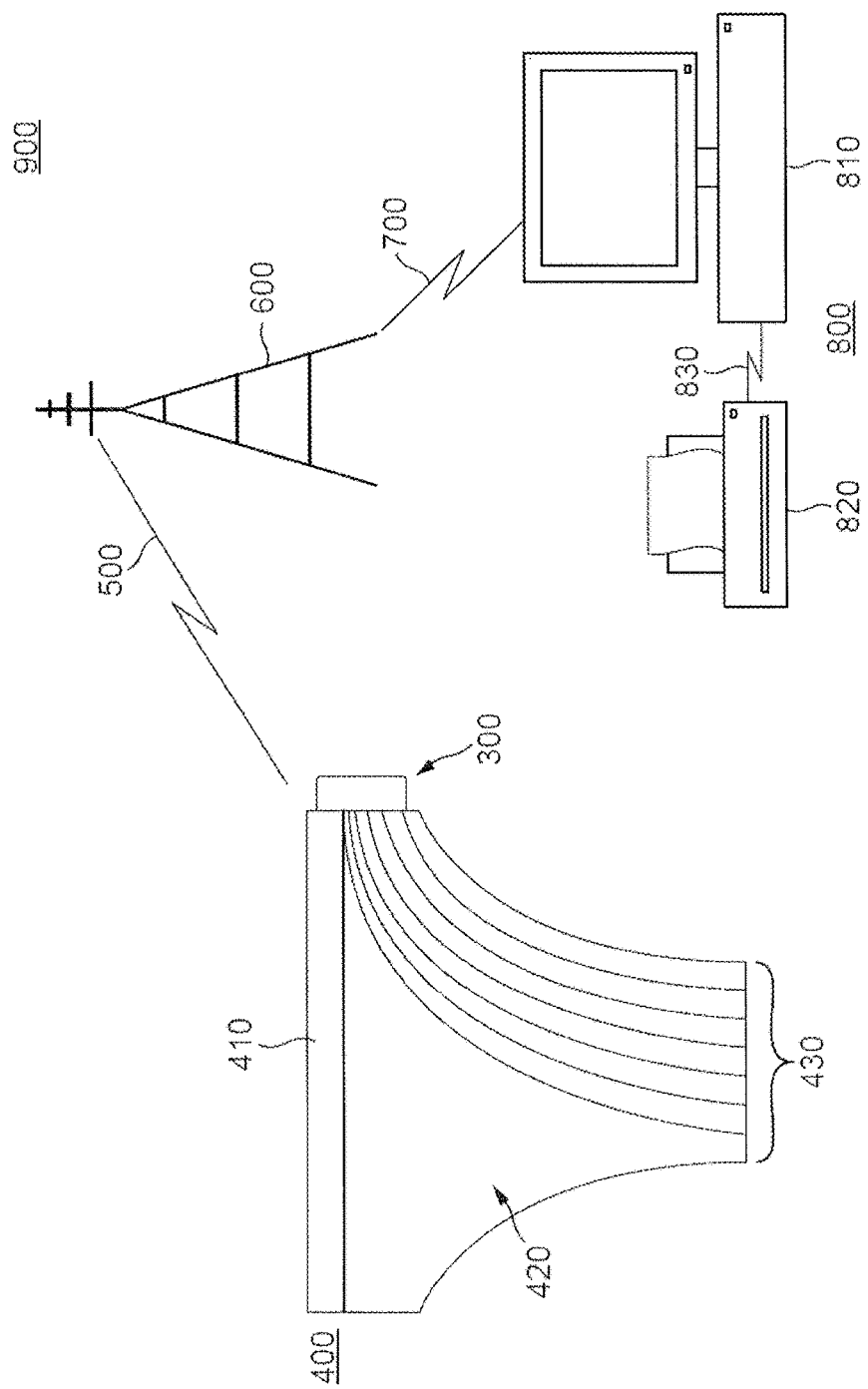
FIG. 1 is a schematic view of a monitoring system for absorbent articles.

In the system of FIG. 1, the logger unit may be disposable with the absorbent article. It therefore may be provided with a single-use internal power source, such as a battery, for powering the datalogging and data transmission electronics. In such a situation, the interval between the absorbent article 400 requiring replacement may be comparable with or only slightly less than the service life time of the internal power source, for reasons of economy.

However, such a configuration, in which the logger unit is disposed with the absorbent article, may be viewed as wasteful and expensive. Therefore, one alternative possibility is to provide a logger unit which is separable from the absorbent article and which may be reconnectable to a fresh, replacement article to continue the logging process for a given individual. Since the sensors 430 should be embedded in the absorbent article in regions which will experience a flow event, for hygiene reasons it may be advantageous to provide new sensor elements together with replacement absorbent articles, while the logger unit, for reasons of cost, is reused.

However, in such a configuration, the lifetime of the internal power source of the logger unit is likely to be far shorter than the service life of the logger unit itself. Periodic replacement or recharging of the power source is likely to be required.

In battery-powered electronic devices, it is conventional for the user of such a device to be actively notified at a point in time at which the remaining useable energy in the power source has dropped to or below a predetermined level, so that replacement and/or recharging action can be undertaken.

However, it is an important goal in the design and construction of sanitary articles that the articles should be as unobtrusive in use as possible. Generally, it is not the user, but the caregiver who should be notified in the event of such a power source condition. Especially if the user of the absorbent article is an infant, an individual affected by dementia, or similar, in such situations the presence of a low battery notification or similar on a datalogger is likely to distract the user, or to cause them to investigate the datalogger, potentially causing damage, inadvertent disconnection, or simply anxiety. Further, the caregiver may not be present at the moment when the low power source condition arises, and the user may not be in a position to react appropriately, for example by undertaking replacement or recharging action for the power source.

One embodiment of the present disclosure is able to provide such a low battery notification to a caregiver without needlessly or undesirably alerting the user of the absorbent article.

Figure 2:
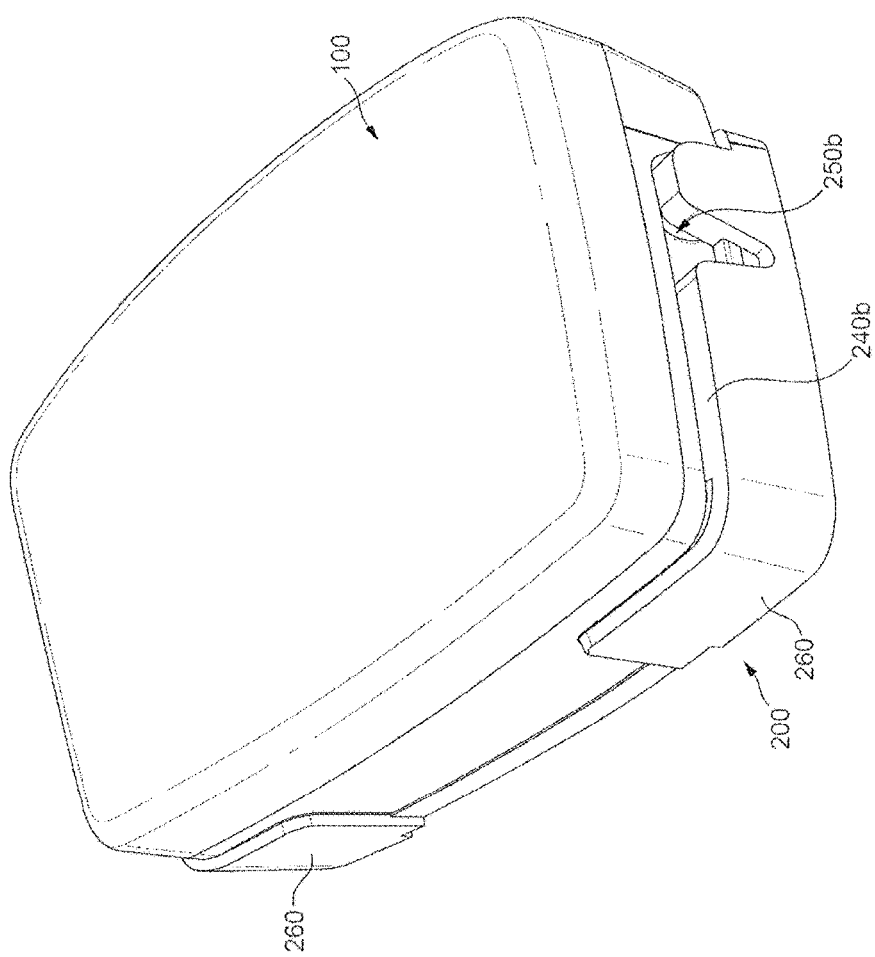
FIG. 2 is an electronics enclosure engaged with a receptacle.

As shown in FIG. 2, the datalogger of the present embodiment is housed within an electronics enclosure 100, which is able to co-operate with a receptacle 200 to be engaged with and retained therein. The receptacle is provided to the absorbent article, and contacts on the lower surface of the electronics enclosure (not shown in FIG. 2) are arranged to come into contact with terminal contacts at the receptacle which are electrically connected to, or formed as conductive portions of, the sensor elements. In such a way, the electronics enclosure may be easily transferred between absorbent articles when the absorbent article requires replacement while being reliably retained on the absorbent article in electrical connection with the sensor elements.

Figure 3:
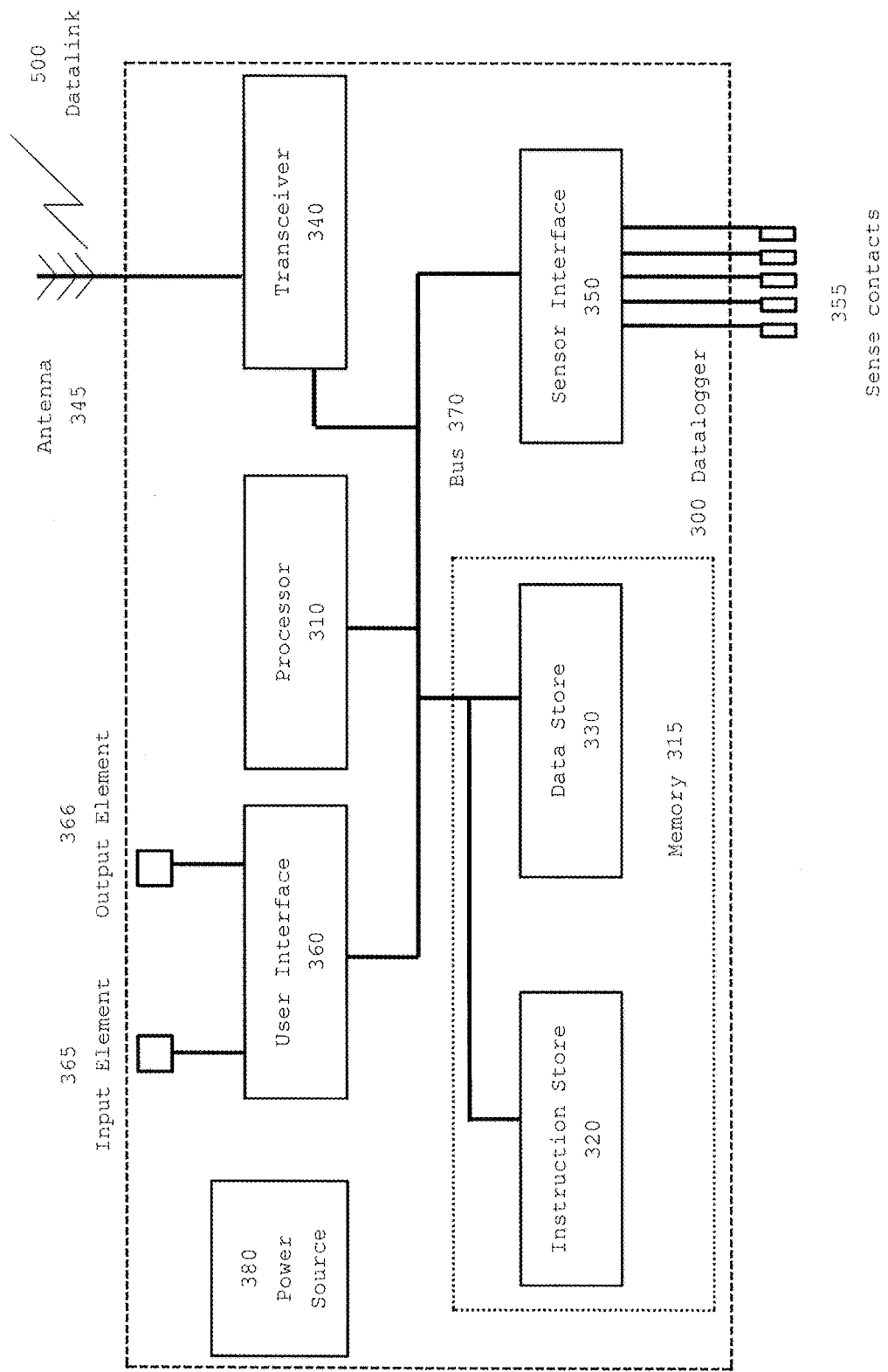
FIG. 3 is a schematic diagram of a datalogger being an embodiment of the present disclosure.

Inside electronics enclosure 100 is data processing equipment depicted in schematic form in FIG. 3. However, it is important to understand that the configuration shown in FIG. 3 is purely exemplary, and the functionality provided by the arrangement of FIG. 3 may be provided in other ways, including using application specific integrated circuits (ASICs), general purpose data processors, discrete electronics, or other arrangements as are conventional in the art.

As an example of the configuration of data processing equipment which provides the functionality of datalogger 300, there is provided a processor 310, which derives instructions from instruction store 320, operates on data stored in data store 330, is able to transmit and receive data over data link 500 using transceiver 340 and antenna 345, is able to interface with the sensor elements in the absorbent article by means of sensor interface 350 and sensor contacts 355, and is able to give and receive user interface events via user interface 360 connected to input element 365 and output element 366.

Processor 310, instruction store 320, data store 330, transceiver 340, sensor interface 350, and user interface 360 are connected by a common bus 370 and are all powered by power source 380.

The instruction store 320 and data store 330 may be implemented as a common memory 315, or may be implemented as individual memories.

Power source 380 can be provided, for example, as any suitable power source such as a lithium ion or nickel metal hydride rechargeable battery, or a user-replaceable zinc or alkaline battery.

Sensor interface 350 may be, for example, an analogue to digital convertor (ADC) configured to measure resistance, conductivity or capacitance between pairs of sense contacts 355, or may be a threshold sensing unit configured to detect when the resistance, conductivity or capacitance between pairs of sense contacts 355 drops below or rises above a predetermined level.

Aside from detecting resistance between sense contacts 355, sensor interface 350 may also be configured to detect, in combination with suitable active or passive sense elements as may be known in the art, other variables, parameters or properties, such as pH, temperature, and the presence or absence of certain compounds in the absorbent article.

Input element 365 may be, for example, a button, a switch, a touch panel, an accelerometer, or a light level sensor, while output element 366 may be, for example, a visible indicator such as a lamp or LED; an audible indicator such as a sounder, buzzer, beeper, or loudspeaker; or a tactile indicator such as a vibrator.

One mode of operation of the datalogger 300 will now be described, with reference to the state diagram of FIG. 4.

While the logger is connected to the absorbent article, it is in state S1, which in the present configuration corresponds to a normal datalogging condition. In this condition, the processor queries the sensor interface at intervals and records the results in data store 330. At intervals greater than or equal to the intervals at which processor 310 receives information from sensor interface 350, the data stored in data store 330 is transmitted via transceiver 340 over data link 500, and, if the transmission is determined to be successful, the data is deleted from the data store 330. For example, the sensor interface may be queried for data every second while transmission of data via transceiver 340 may occur, for example, every twenty minutes. Of course these values can be changed depending on the size of data store 330, the costs associated with data transmission over data link 500 and the network environment within which transceiver 340 operates. Particularly, in a cellular network environment, the costs of using data link 500 may be per session, rather than per unit of data, and therefore it may be more economical to provide a larger data store 330 and a longer period before transmission of data over transceiver 340. In contrast, if data link 500 is provided as a high-capacity wireless Ethernet network, for example, to ensure that the incontinence management system has the most recent data available to users, it may be preferred to transmit data over the data link as frequently or almost as frequently as data is received by the processor from the sensor interface 350.

When the attention of the caregiver is drawn to the fact that an absorbent article requires replacement, whether by the incontinence management system itself, on request of a user, or at, for example, a scheduled replacement interval determined in accordance with a user's care plan, datalogger enclosure 100 may be removed from receptacle 200, and processor 310 may be able to sense, for example by a change in electrical parameters, such as capacitance of sense contacts 355, that the logger has been disconnected from the absorbent article. In some cases, when the enclosure 100 is engaged with receptacle 200, certain of contacts 355 of datalogger 300 will always be in a short-circuit condition, for example by corresponding to short-circuited contacts in the receptacle. By detecting an open-circuit condition on the corresponding sense contacts, the datalogger may be able to detect that a datalogger disconnection event has occurred. Other methods of detecting a datalogger disconnection event are via, for example, a microswitch provided as one of input elements 365 which is arranged to change state when the enclosure 100 is removed from receptacle 200, a reed switch or magnetic sensor which is arranged to change state when taken out of proximity of a corresponding magnet in the receptacle or absorbent article, an optical sensor such as a light level sensor provided as one of the input elements 365 which changes from a dark state to a light state when enclosure 100 is removed from receptacle 200, or a button push event detected by a push button as one of input elements 365 which is manually operated by the user to signal that a disconnection event has occurred. Rather than activation of a push button, activation of another user interface input element could be used to transition from the datalogging state.

For the purposes of discussion, it is assumed that the disconnection event has been determined by the existence of an open-circuit condition between two of sense contacts 355. On determination of this condition, represented by event A in FIG. 4, the datalogger 300 exits state S1, the datalogging condition, as the first operating condition, and enters state S2, being a second operating condition, and here being a notification condition. In the notification condition, one or more of the output elements 366 may be activated, in some circumstances in different patterns, to signal a particular status or combination of statuses of the datalogger 300. For example, a visible indicator may be activated to indicate that replacement or recharging of the power source 380 is required. Aside from activation of a visible indicator, other methods as mentioned previously with reference to output element 366 may be used to provide notification to the caregiver of the status of datalogger 300. In particular, audible or tactile methods may be used in the notification condition, so that the caregiver need not be looking at the enclosure 100 during or after the disconnection event to determine that a particular status exists. This may be advantageous when the disconnection event occurs during a care process, such as removal, disposal and replacement of the absorbent article.

Combinations or patterns of activation of output elements 366 may be used to signal different statuses. For example, a tactile element such as a vibrator may be activated to inform the caregiver that a status requiring caregiver action is required, with a combination of illuminated elements at different locations on the enclosure 100 or of different colours indicating the nature of the status. For example, a particular colour could be associated with low battery events.

Alternatively or additionally, different patterns, such as frequency and length of activation of the output elements 366 may be used to convey different statuses to the caregiver. For example, a pulsed illumination, vibration or sound may indicate that replacing or recharging the power source 380 is advisable, while continuous illumination, vibration or sounding may indicate that replacement or recharging of power source 380 is urgent. Such patterned notification activity, despite being able to attract the attention of the caregiver, is not likely to alarm the user or attract undesired attention to the absorbent article, since the notification condition is entered when the disconnection event is determined and thus when the enclosure is likely to be in the hands of the caregiver. Thus it is possible to ensure that the notification condition is entered only when the situation is under the control of the caregiver.

One implementation of such a condition could be to indicate that replacement of power source 380 is advisable when a first predetermined remaining energy level, such as 50% of maximum capacity, is reached, while indication that replacement is urgent could be signalled when a further predetermined level, such as 20% is reached.

In addition to battery status, other statuses which may be of use or interest to the caregiver may also be signalled on a disconnection event. For example, an error status requiring maintenance or replacement of the datalogger could be signalled by another pattern of activation of output elements 366. For example, a rapidly blinking visible indicator could indicate to the caregiver that an error status had developed during the proceeding datalogging period, and that the datalogger 300 should be taken out of service.

Further statuses that might require caregiver intervention, and which could be indicated during the notification condition, could include a temporary failure of the data link 500. Particularly, in some circumstances, datalogger 300 may be configured, if transmission of data stored in data store 330 over data link 500 is not reliably possible, such that data may continue to accumulate in data store 330. Transceiver 340 may then seek to re-establish data link 500, either continuously or at predetermined intervals. Once data link 500 is re-established, all data remaining in data store 330 may be transmitted over data link 500 before the data is erased. Such a situation may occur, for example, while using a cellular data connection as data link 500 in areas of poor cellular coverage.

Under some circumstances, the failure of data link 500 may persist, and data will continue to accumulate in data store 330. Under such a condition, it is important that datalogger 300 is relocated to an area of sufficiently good signal strength for re-establishment of data link 500 before the capacity of data store 330 is exceeded. Accordingly, one possible status which could be notified to a caregiver after a disconnection event via an appropriate activation of output elements 366 is that the datalogger should be removed to an area having good signal coverage to enable data download to take place.

Once the second operating condition, the notification condition, is entered, the device may remain in the notification condition until a further event. In some circumstances, the further event may be an external event such as reconnection of the datalogger to a receptacle 200 connected to a further absorbent article, after which further event the datalogger returns to the datalogging condition. Such a further event could be signalled in a similar way as the disconnection event, either automatically by sensing reconnection of the enclosure to the receptacle, or manually by activation of a user interface element. Other behaviours are also, however, possible.

For example, the status notification condition may, to save power or to avoid unnecessary or ongoing disturbance to the caregiver, transition from the status notification condition, in which output elements 366 are activated according to the status to be notified, to a standby condition in which no output element is activated and during which no datalogging or data link activity takes place. As shown in FIG. 4, the standby condition, represented in FIG. 4 by S3, is a third cooperating condition which is initiated on a further event, event B. Event B may be an internal event, such as the completion of a specified notification sequence, the expiry of a timer, or a change in the status of one of the operating elements of the datalogger such as power source 380 having been replaced or recharged or data link 500 having been re-established and residual data in data store 330 having been transmitted. The nature of the event required to transition from the notification condition may depend on the status being notified. For example, a low battery notification condition may persist for a short period of time, but a serious failure condition may cause the notification period to be extended indefinitely.

Even, activation of a user interface input element 365 may be assigned as the event to transition from the second, notification, operating state to the third, standby, operating state, such as the activation of an acknowledgment user interface element provided to enclosure 100. For example, an acknowledgment button may be pressed or the device may be shaken to activate an accelerometer event.

Figure 4:
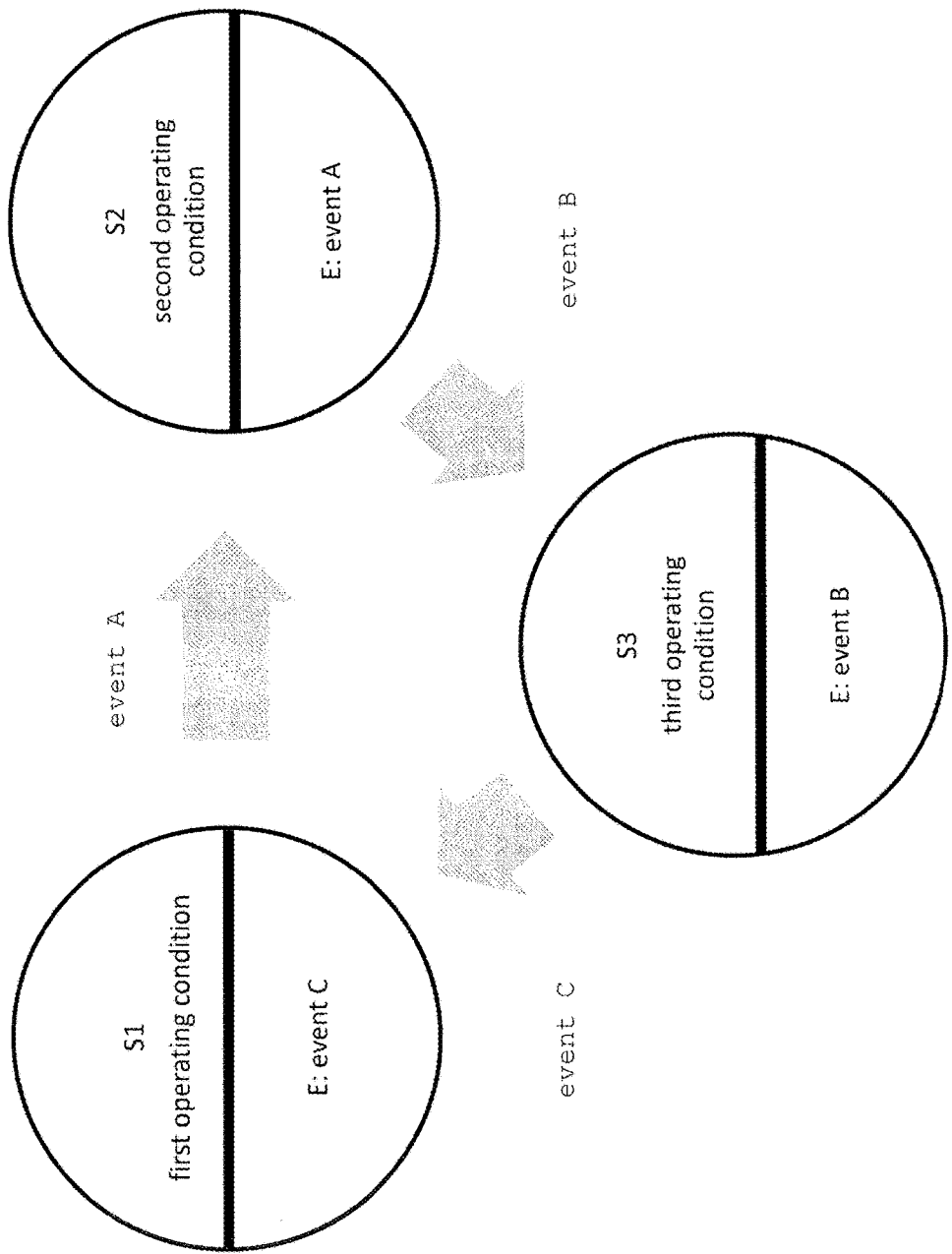
FIG. 4 is a state diagram being an implementation of the present disclosure.

Once in the standby state, represented as the third operating condition S3, a further event, shown as event C in FIG. 4, may be used to return the datalogger to the first, datalogging, operating condition S1. For example, a connection event, in which the datalogger is inserted into a receptacle and thus connected to an absorbent article, may be detected by a sensor interface 350, which would cause the datalogger 300 to transition from the third, standby, operating condition S3 to the first, datalogging, operating condition S1.

In the same way as for a disconnection event, other methods of detecting a datalogger connection event are via, for example, a microswitch provided as one of input elements 365 which is arranged to change state when the enclosure 100 is engaged with receptacle 200, a reed switch or magnetic sensor which is arranged to change state when brought into proximity of a corresponding magnet in the receptacle or absorbent article, an optical sensor such as a light level sensor provided as one of the input elements 365 which changes from a light state to a dark state when enclosure 100 is engaged with receptacle 200, or a button push event detected by a push button as one of input elements 365 which is manually operated by the user to signal that a connection event has occurred. The push button may be the same push button as used to signal a disconnection event, of may be a further push button. Rather than activation of a push button, activation of another user interface input element could be used to transition to the datalogging state.

Direct transition from the notification condition to the datalogging condition may also be possible, either on the same condition for transitioning from the standby event to the datalogging condition, or on a different condition, for example additionally requiring activation of an acknowledgement or override user interface input element 365.

In such a way, notification to the user can be provided in a timely and useful manner without damaging the unobtrusiveness of the absorbent article or without causing needless anxiety to the user.

However, using the event-driven concept of the preceding embodiment, other functionality is also possible. For example, the second operating condition need not be a notification condition, but could be a standby condition, in which a low power state of processor 310 is entered, or a data transmission condition, in which accumulated data during the logging period is transmitted over data link 500 out of the normal schedule for such transmissions. In one variant, data store 330 is sufficiently sized to record all data occurring during the usage life of an absorbent article, and data transmission is only effected on detection of a disconnection event. Such may, for example, reduce the running costs of the system in terms of data link costs.

Also, using the concept of event-driven state changes in such a datalogger, other events aside from disconnection or connection from an absorbent article or user interaction events may be used to change states in the datalogger. For example, a further pair of contacts on enclosure 100 can be used, for example by detecting the presence of a voltage or a closed-circuit condition, to determine that the datalogger is connected to a charging station. The charging station may typically be sited in a location having relatively good conditions for establishment of data link 500. Accordingly, on connection of datalogger 300 to the charging station, as well as power source 380 being connected to a charging station for replenishment of the energy stored in power source 380, datalogger 300 can be put into a flush condition, in which any data stored in data store 330 is transmitted via transceiver 340 and data link 500 in a reliable manner. After the transmission is completed, the state may further change from the data store flush state to the standby state while power source 380 is charged.

Figure 5:
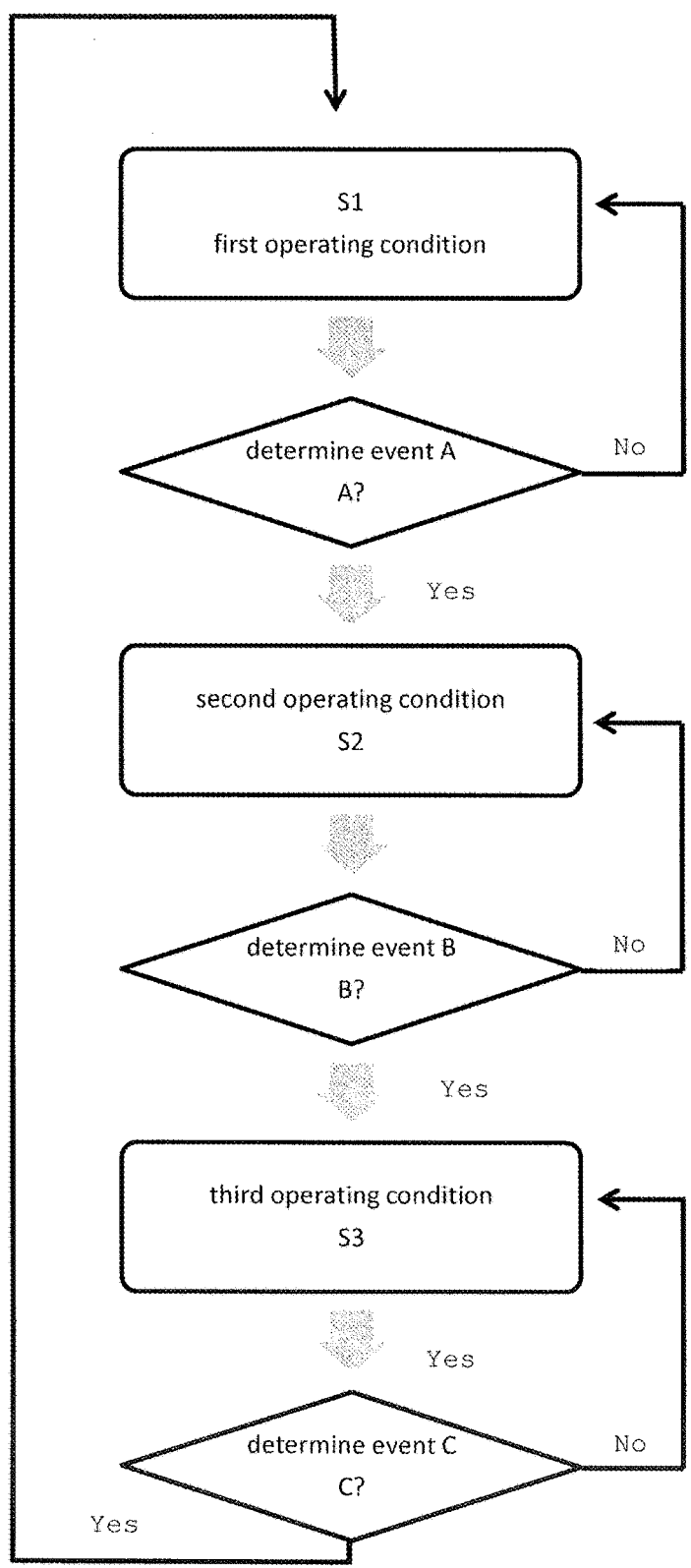
FIG. 5 is a flow chart showing an implementation of the state diagram of FIG. 4.

In the above, the various operating states of datalogger 300 may be implemented as programmatic states or routines of processor 310. Transitions between the states can then be interrupt-driven or can be driven via polling of the relevant components of datalogger 300. Such a situation is represented as a flow diagram in FIG. 5. Assuming that the datalogger is in the first operating condition S1, the processor polls each relevant device, such as transceiver 340, sensor interface 350, or user interface 360, to determine whether an event, such as event A, has occurred. If no event has occurred, the processor continues to operate in its first condition. However, if, when polled, an element of datalogger 300 indicates that event A has occurred, the operating condition of processor 310 advances to the second operating condition S2. The processor remains in this condition, polling the relevant elements to determine whether an event B has occurred. Once the processor determines that event B has occurred, the state of the processor advances to the third operating condition S3. While the processor remains in the third operating condition, it repeatedly polls the relevant elements to determine whether a third event, event C, has occurred, and again, once the processor establishes that event C has occurred, the processor returns to the first operating condition S1. Polling may be carried out at the level of processor cycles, programmatic loops, or at intervals of time. Further, the polling rate may differ between the operating conditions; specifically, if an operating state is a standby state, it may be desirable to reduce the frequency with which polling of the elements occurs to conserve power.

Although specific examples have been described above, fewer or more than three operating conditions may be implemented. For example, the third operating condition can be identical with the first operating condition. Alternatively, fourth, fifth, sixth, and so on, operating conditions may be provided, each with their proper entry and exit events. Branching may be implemented, such that, from a first operating condition such as standby state, different states, such as a notification condition or a data transmission condition may be entered depending on determination of different events. Furthermore, each state may include a variety of sub-states, which may be simultaneous, such as notification of two different statuses at the same time in a notification condition, or may be sequential, such as the transmission of data remaining in the data store 330 followed by erasure of the data from data store 330 in a flush condition.

In the above, connection and disconnection events have been described with reference to physical connection or disconnection of an enclosure associated with the datalogger with a receptacle provided on the absorbent article or with reference to electrical connection or disconnection between contacts on the datalogger and contacts on the absorbent article. However, in the present disclosure, connection and disconnection events can also refer to establishment and dis-establishment of an operative contactless connection between the datalogger and a remote sensor. For example, a sensor, such as moisture sensor or a gas sensor, can be provided in the form of a passive resonant circuit coupled to an antenna, whose resonant electrical characteristics, for example resonant frequency, will change with sensor state. A connection or disconnection event, in such a case, can include detection by the datalogger of whether such a circuit is near, for example, whether the datalogger has been brought near to such a circuit to form an operative connection such that the state of the resonant circuit may be determined. Alternatively, the sensor can be provided in the form of active electrical circuit coupled to an antenna, for example an RFID tag, and the connection or disconnection event, in such a case, can include detection by the datalogger whether or such a circuit is sufficiently near for communication. In each case, the connection or disconnection is such as to cause a change in state of an electrical circuit of the datalogger that is responsive to an external event. All such arrangements are considered to be within scope of the terms connection and disconnection event as used herein.

Embodiments of the present disclosure may thus provide a datalogging method, a datalogger, or an incontinence management system which is flexible, which is unobtrusive, and which is easy to use even by relatively untrained caregivers. Such a system may find application in residential homes, medical facilities, childcare facilities, schools, corrective facilities, and other environments where the monitoring of the continence status of one individual or a plurality of individuals is required.

The foregoing embodiments and their variants have been disclosed for illustrative purposes only, and further variation is wholly possible within the capabilities of the skilled reader. Accordingly, the appended claims are intended to cover all modifications, substitutions, alterations, omissions and additions which one skilled in the art could achieve from the foregoing disclosure, taking into account his own general and specialist knowledge and expertise.

The invention claimed is:

1. A method of operating a battery-powered datalogger comprising at least one tactile, audible or visible output element and adapted for logging sensor data from an absorbent article having at least one sensor element, the method comprising:
   determining an external event, wherein the external event comprises a disconnection event in which the datalogger is disconnected from the at least one sensor element in the absorbent article; and
   on determination of the external event, transitioning from a first operating condition to a second operating condition, wherein the second operating condition comprises a status notification condition in which the at least one tactile, audible or visible output element housed in an electronics enclosure of the datalogger is activated to signal a low battery status of the datalogger.

2. The method according to claim 1, wherein the first operating condition is at least one condition selected from the group consisting of: a datalogging condition; a standby condition; and a data transmission condition.

3. The method according to claim 2, wherein the first operating condition includes the datalogging condition, which comprises the transmission of sensor data over a data link.

4. The method according to claim 2, wherein the first operating condition includes the datalogging condition and the data transmission condition,
   wherein the datalogging condition comprises the storage of sensor data in a memory internal to the datalogger and the transmission of stored sensor data at predetermined intervals over a data link, and
   wherein the data transmission condition is a flush condition in which sensor data stored in the memory is transmitted over the data link at other than a predetermined interval of the datalogging condition.

5. The method according to claim 1 further comprising transitioning from the second operating condition to a third operating condition on determination of a further event.

6. The method according to claim 5, wherein the further event is at least one internal event selected from the group consisting of: an expiry of a timer associated with the second operating condition; a completion of a process associated with the second operating condition; and a change in status of an internal device.

7. The method according to claim 5, wherein the further event is at least one external event selected from the group consisting of: a connection event in which the datalogger is connected to an absorbent article; a charge event in which the datalogger is connected to a charging station; and a user interaction event in which the user interacts with a user interface element of the datalogger.

8. The method according to claim 1, wherein the determination of the external event comprises detection of a change in state of an electrical circuit of the datalogger that is responsive to an external event.

9. The method according to claim 1, wherein the determination of the external event comprises detection of at least one event selected from the group consisting of: a change in state of at least one electrical contact on the exterior of the datalogger; a change in state of at least one sensor on the exterior of the datalogger; a change in state of at least one switch on the exterior of the datalogger.

10. A battery-powered datalogger adapted for logging sensor data from an absorbent article having at least one sensor element, the datalogger comprising:
an electronics enclosure, which houses:
a processor configured to determine an external event and, on determination of the external event, to transition from a first operating condition to a second operating condition; and
at least one tactile, audible or visible output element,
wherein the external event is a disconnection event in which the datalogger is disconnected from the at least one sensor element in the absorbent article, and
wherein the second operating condition is a status notification condition in which the at least one tactile, audible or visible output element is activated to signal a low battery status of the datalogger.

11. The datalogger of claim 10, wherein the first operating condition comprises a condition selected from the group consisting of: a datalogging condition; a standby condition; and a data transmission condition.

12. The datalogger of claim 11, further comprising a transmitter and wherein the first operating condition comprises the datalogging condition, wherein the datalogging condition comprises the transmission of sensor data over a data link.

13. The datalogger according to claim 11, further comprising: a memory adapted to store sensor data; and a transmitter,
wherein the first operating condition includes the datalogging condition and the data transmission condition,
wherein the datalogging condition comprises the storage of sensor data in the memory and the transmission of stored sensor data at predetermined intervals with the transmitter, and
wherein the data transmission condition is a flush condition in which sensor data stored in the memory is transmitted with the transmitter at other than a predetermined interval of the datalogging condition.

14. The datalogger according to claim 10, wherein the processor is further configured to transition from the second operating condition to a third operating condition on determination of a further event.

15. The datalogger according to claim 14, wherein the further event is at least one internal event selected from the group consisting of: an expiry of a timer associated with the second operating condition; a completion of a process associated with the second operating condition; and a change in status of an internal device.

16. The datalogger according to claim 15, wherein the further event is at least one external event selected from the group consisting of: a connection event in which the datalogger is connected to an absorbent article; a charge event in which the datalogger is connected to a charging station; and a user interaction event in which the user interacts with a user interface element of the datalogger.

17. The datalogger according to claim 10, wherein the external event the processor is configured to determine comprises detection of a change in state of an electrical circuit of the datalogger that is responsive to an external event.

18. The datalogger according to claim 10, wherein the external event the processor is configured to determine comprises detection of at least one event selected from the group consisting of: a change in state of at least one electrical contact on the exterior of the datalogger; a change in state of at least one sensor on the exterior of the datalogger; and a change in state of at least one switch on the exterior of the datalogger.

* * * * *